United States Patent [19]

Yamagami et al.

[11] Patent Number: 5,234,826
[45] Date of Patent: Aug. 10, 1993

[54] BIOLOGICAL PROCESS FOR PREPARING OPTICALLY ACTIVE LACTIC ACID

[75] Inventors: Tomohide Yamagami, Osaka; Etsuko Kobayashi; Takakazu Endo, both of Kanagawa, all of Japan

[73] Assignee: Nitto Chemical Industry Co., Ltd., Tokyo, Japan

[21] Appl. No.: 745,297

[22] Filed: Aug. 15, 1991

[30] Foreign Application Priority Data

Aug. 16, 1990 [JP] Japan ................................. 2-214916

[51] Int. Cl.$^5$ ........................ C12B 7/42; C12B 41/00; C12B 7/56; C07C 59/08
[52] U.S. Cl. ................................. 435/139; 435/280; 435/822
[58] Field of Search ........................ 435/139, 280, 822

[56] References Cited

U.S. PATENT DOCUMENTS 3,940,316  2/1976  Commeyras ........................ 435/139

FOREIGN PATENT DOCUMENTS 0356912  7/1990  European Pat. Off. .
56086  3/1986  Japan .
222696  9/1988  Japan .

OTHER PUBLICATIONS

Derwent Abs. 84-054368/09 Markoy (et al) SU1011630.
Derwent Abs 92-02964/04 Asahi Chem J03277292 (Dec. 1991).
Derwent Abs 86-184583/29 Enomoto et al. GP-187680 (Jul. 1986).

Primary Examiner—Herbert J. Lilling
Attorney, Agent, or Firm—Sughrue, Mion, Zinn, Macpeak & Seas

[57] ABSTRACT

A process for preparing an optically active lactic acid comprising subjecting DL-lactonitrile or acetaldehyde and prussic acid to the action of a microorganism belonging to the genus Enterobacter, Arthrobacter, Caseobacter, Brevibacterium, Aureobacterium, Escherichia, Micrococcus, Streptomyces, Flavobacterium, Aeromonas, Nocardia, Mycoplana, Cellulomonas, Erwinia, Candida, Pseudomonas, Rhodococcus, Bacillus, Alcaligenes, Corynebacterium, Microbacterium or Obsumbacterium, or treated microbial cells thereof, which the microorganism is capable of stereospecifically hydrolyzing a nitrile in a polar solvent. D-Lactic acid or L-lactic acid can be produced directly in a predominant proportion from the starting materials.

5 Claims, No Drawings

BIOLOGICAL PROCESS FOR PREPARING OPTICALLY ACTIVE LACTIC ACID

FIELD OF THE INVENTION

The invention relates to a process for preparing an optically active lactic acid from DL-lactonitrile using a microorganism. An optically active lactic acid is useful as a chiral center for producing optically active pharmaceuticals and agricultural chemicals. For example, D-lactic acid is expected to enjoy an increasing demand as a starting material for L-2-chloropropionic acid, an intermediate of optically active herbicides. Further, increasingly, much study is directed to the use of optically active lactic acid polymers as medical materials.

BACKGROUND OF THE INVENTION

Known processes for biologically preparing lactic acid from DL-lactonitrile include a process of using a microorganism belonging to the genus Bacillus, Bacteridium, Micrococcus or Brevibacterium (see U.S. Pat. No. 3,940,316); a process of using a microorganism belonging to the genus Corynebacterium (see JP-A-61-56086, the term "JP-A" as used herein means an "unexamined published Japanese patent application"); a process of using a microorganism belonging to the genus Corynebacterium, Nocardia, Bacillus, Bacteridium, Micrococcus or Brevibacterium (see JP-A-61-162191); and a process of using a microorganism belonging to the genus Pseudomonas, Arthrobacter, Aspergillus, Penicillium, Cochliobolus or Fusarium (see JP-A-63-222696). Those processes relate to production of racemic lactic acid and not to production of an optically active lactic acid.

On the other hand, with respect to production of optically active hydroxy acids, there are known a process for producing an L-α-hydroxy acid which uses yeast of the genus Torulopsis (see JP-B-54-14668, the term "JP-B" as used herein means an "examined published Japanese patent application") and a process for producing an optically active α-substituted organic acid which uses a microorganism belonging to the genus Alcaligenes, Pseudomonas, Rhodopsuedomonas, Corynebacterium, Acinetobacter, Bacillus, Mycobacterium, Rhodococcus or Candida (see EP 0348901A). However, those processes do not make it possible to obtain a desired optically active compound in a predominant proportion from a starting racemate. Further, these are no illustrative examples concerning the preparation of an optically active lactic acid from DL-lactonitrile and thus, it is unclear whether an optically active lactic acid can be prepared with high efficiency and at a high optical purity by those processes.

SUMMARY OF THE INVENTION

Accordingly, an object of the present invention is to provide an industrially advantageous process for preparing an optically active lactic acid from DL-lactonitrile.

The inventors have conducted extensive investigation into that problem. As a result, they have found that an optically active lactic acid can be obtained efficiently by subjecting DL-lactonitrile to the action of a specific microorganism capable of asymmetrically hydrolyzing a nitrile in a polar solvent. The inventors have ascertained that lactonitrile has the property of coming to equilibrium upon dissociation into acetaldehyde and prussic acid in a polar solvent, which eventually leads to racemization. Thus, a desired optically active lactic acid can be prepared in a predominant proportion directly from DL-lactonitrile by combining such a racemization system with a nitrile asymmetric hydrolase produced from a microorganism. It is possible theoretically to convert all the starting materials to a desired optically active lactic acid. The present invention has been completed based on those findings.

The present invention relates to a process for preparing an optically active lactic acid comprising subjecting DL-lactonitrile to the action of a microorganism belonging to the genus Enterobacter, Arthrobacter, Caseobacter, Brevibacterium, Aureobacterium, Escherichia, Micrococcus, Streptomyces, Flavobacterium, Aeromonas, Nocardia, Mycoplana, Cellulomonas, Erwinia, Candida, Pseudomonas, Rhodococcus, Bacillus, Alcaligenes, Corynebacterium, Microbacterium or Obsumbacterium, or treated microbial cells thereof, which said microorganism is capable of stereospecifically hydrolyzing a nitrile in a polar solvent to produce directly D-lactic acid or L-lactic acid in a predominant proportion to said starting DL-actonitrile.

In another embodiment, the DL-lactonitrile starting material is replaced by prussic acid and acetaldehyde.

DETAILED DESCRIPTION OF THE INVENTION

The microorganism used in the present invention is a microorganism belonging to the genus Enterobacter, Arthrobacter, Caseobacter, Brevibacterium, Aureobacterium, Escherichia, Micrococcus, Streptomyces, Flavobacterium, Aeromonas, Nocardia, Mycoplana, Cellulomonas, Erwinia, Candida, Pseudomonas, Rhodococcus, Bacillus, Alcaligenes, Corynebacterium, Microbacterium or Obsumbacterium, which is capable of stereospecifically hydrolyzing a nitrile. Those microorganisms can be obtained, for example, by the following process.

(1) Isolation of Strains

The soil collected at Yokohama-shi of Kanagawa, Japan is suspended in 15 ml of a sterilized water and allowed to stand for 30 minutes. Then, 0.1 to 0.2 ml of the resulting supernatant is sprayed on an agar medium containing 2-chloropropionitrile as a nitrogen source (20 g of glycerol, 1 g of 2-chloropropionitrile, 3 g of $K_2HPO_4$, 0.2 g of $MgCl_2$, 40 mg of $CaCl_2$, 4 mg of $MnSO_4.4H_2O$, 0.7 mg of $FeCl_3.7H_2O$; 0.1 mg of $ZnSO_4.7H_2O$ and 15 g of agar in 1 l of demineralized water (pH 7.0) and then cultured at 30° C. for 5 to 6 days. The colonies formed are purely isolated on the agar medium.

(2) Assay of Activity

The thus-obtained strains are cultured in the same manner as in Example 1 below and reacted with a lactonitrile. After completion of the reaction, the system is subjected to centrifugation to remove the microbial cells. The supernatant liquor is analyzed by liquid chromatography (column: SHODEX ODS F511A, carrier: 0.2M $H_3PO_4$, column temp.: 30° C., monitor wavelength: 208 nm) to determine an amount of lactic acid produced.

In addition, its optical purity is determined in the same manner as in Example 1 below.

Specific examples of microorganisms which can be used in the present invention include Enterobacter sp.

SK12 (FERM No. BP-3322), *Enterobacter taylorae* JCM 3943, Arthrobacter sp. SK103 (FERM No. P-11300), Arthrobacter sp. HR1 (FERM No. BP-3323), *Arthrobacter oxydans* IFO 12138, Caseobacter sp. BC4 (FERM No. BP-3316), Caseobacter sp. BC23 (FERM No. P-11261), *Brevibacterium acetylicum* IAM 1790, *Brevibacterium helvolum* ATCC 11822, *Aureobacterium testaceum* IAM 1561, *Escherichia coli* IFO 3301, *Micrococcus luteus* ATCC 383, *Micrococcus varians* IAM 1099, *Micrococcus roseus* IFO 3768, *Strectomyes griseus* IFO 3355, *Streptomyes griseus* IFO 14059, *Flavobacterium flavescens* ATCC 8315, Flavobacterium sp. SK150 (FERM No. P-11645), *Aeromonas punctata* IFO 13288, *Nocardia calcarea* KCC A0191, *Nocardia polychromogenes* IFM 19, *Mycoplana dimorcha* ATCC 4279, *Cellulomonas fimi* IAM 12107, *Erwinia herbicola* IFO 12686, *Candida guilliermondii* IFO 0566, *Candida lypolytica* IAM 4964, Pseudomonas sp. SK13 (FERM No. BP-3325), Pseudomonas sp. SK31 (FERM No. P-11310), Pseudomonas sp. SK87 (FERM No. P-11311), Pseudomonas sp. BC13-2 (FERM No. BP-3319), Pseudomonas sp. BC15-2 (FERM No. BP-3320), *Pseudomonas synxantha* IAM 12356, *Pseudomonas aerucinosa* IAM 1267, *Pseudomonas ovalis* IAM 1002, *Rhodococcus erythropolis* IFO 12540, *Rhodococcus erythropolis* IFO 12320, Rhodococcus sp. SK92 (FERM No. BP-3324), Rhodococcus sp. HR11 (FERM No. P-11306), Rhodococcus sp. SK70 (FERM No. P-11304), *Rhodococcus erythropolis* IFO 12538, *Rhodococcus erythropolis* IFO 12539, *Rhodococcus erythropolis* IFM 132, *Rhodococcus erythropolis* IFM 155, *Rhodococcus rhodochrous* ATCC 12674, *Bacillus licheniformis* IFO 12197, *Bacillus licheniformis* IFO 12199, *Bacillus mecaterium* ATCC 25833, *Bacillus subtilis* ATCC 21697, Alcaligenes sp. BC20 (FERM No. P-11264), *Corynebacterium flavescens* IAM 1642, *Microbacterium lacticum* IAM 1640 and *Obsumbacterium proteus* ATCC 12841, and variants of those strains.

Of those strains, *Arthrobacter oxydans* IFO 12138, *Brevibacterium acetylicum* IAM 1790, *Brevibacterium helvolum* ATCC 11822, *Aureobacterium testaceum* IAM 1561, *Escherichia coli* IFO 3301, *Micrococcus luteus* ATCC 383, *Micrococcus varians* IAM 1099, *Micrococcus roseus* IFO 3768, *Streptomyces griseus* IFO 3355, *Streptomyces griseus* IFO 14059, *Flavobacterium flavescens* ATCC 8315, *Aeromonas punctata* IFO 13288, *Nocardia calcarea* KCC A0191, *Nocardia polychromogenes* IFM 19, *Mycoplana dimorpha* ATCC 4279, *Cellulomonas fimi* IAM 12107, *Erwinia herbicola* IFO 12686, *Candida guilliermondii* IFO 0566, *Candida lypolytica* IAM 4964, *Pseudomonas synxantha* IAM 12356, *Pseudomonas aeruginosa* IAM 1267, *Pseudomonas ovalis* IAM 1002, *Rhodococcus erythropolis* IFO 12540, *Rhodococcus erythropolis* IFO 12320, *Rhodococcus erythropolis* IFO 12538, *Rhodococcus erythropolis* IFO 12539, *Rhodococcus erythropolis* IFM 132, *Rhodococcus erythropolis* IFM 155, *Rhodococcus rhodochrous* ATCC 12674, *Bacillus licheniformis* IFO 12197 *Bacillus licheniformis* IFO 12199, *Bacillus megaterium* ATCC 25833, *Bacillus subtilis* ATCC 21697, *Corynebacterium flavescens* IAM 1642, *Microbacterium lacticum* IAM 1640 and *Obsumbacterium proteus* ATCC 12841 are known strains that are available from the American Type Culture Collection (ATCC), the Institute for Fermentation, Osaka (IFO); the Research Institute for Chemobiodynamics, The University of Chiba (IFM); the Institute of Applied Microbiology, The University of Tokyo (IAM); the Tokyo Research Laboratories, Kaken Pharmaceutical Co., Ltd. (KCC); and the Japan Collection of Microorganisms, RIKEN (JCM) under the deposit number listed above.

Other microorganisms are new strains isolated from nature by the present inventors and have been deposited with the Fermentation Research Institute, Agency of Industrial Science & Technology under the respective deposit number (FERM Nos.) listed above. The morphologic and physiologic properties of the new strains are described below.

| SK12: | |
|---|---|
| Shape | bacillus |
| Gram's stain | − |
| Spore | − |
| Mobility | + |
| Oxidase | − |
| Catalase | + |
| O-F test | F |
| Production of gas from glucose | − |
| Indole production | − |
| Methyl Red | + |
| V-P | − |
| Utilization of citric acid | + |
| Production of hydrogen sulfide | − |
| Decomposition of urea | − |
| Deamination reaction of phenylalanine | + |
| Decarboxylation reaction of lysine | − |
| Arginine dehydrolase | − |
| Decarboxylation reaction of ornithine | − |
| SK103 and HR1: | |
| Shape | polymorphic bacillus |
| Gram's stain | + |
| Spore | − |
| Mobility | − |
| Oxidase | − |
| Catalase | + |
| Existence of quinone | MK-9 (H2) |
| Rod-coccus cycle | + |
| Extension of peripheral cells of colony | not observed |
| Growth under anaerobic condition | − |
| Diamino acid of cell wall | lysine |
| Glycolyl test | − (acetyl type) |
| Sugar composition of cell wall: | |
| Arabinose | − |
| Galactose | − |
| BC4 and BC23: | |
| Shape | polymorphic bacillus |
| Gram's stain | + |
| Spore | − |
| Mobility | − |
| Flagellum | − |
| Oxidase | − |
| Catalase | + |
| Existence of quinone | MK-8 (H2) |
| Rod-coccus cycle | + |
| Extension of peripheral cells of colony | not observed |
| Growth under anaerobic condition | − |
| Diamino acid of cell wall | meso-diaminopimelic acid |
| Glycolyl test | − (acetyl type) |
| Sugar composition of cell wall: | |
| Arabinose | + |
| Galactose | + |
| SK150: | |
| Shape | bacillus |
| Gram's stain | − |
| Spore | − |
| Mobility | − |
| Flagellum | − |
| Oxidase | + |
| Catalase | + |
| O-F test | O |

| -continued | |
|---|---|
| SK13, SK31, SK87, BC13-2, and BC15-2: | |
| Shape | bacillus |
| Gram's stain | − |
| Spore | − |
| Mobility | + |
| Flagellum | polar |
| Oxidase | + |
| Catalase | + |
| O-F test | O |
| SK92, HR11, and SK70: | |
| Shape | polymorphic bacillus |
| Gram's stain | + |
| Spore | − |
| Mobility | − |
| Oxidase | − |
| Catalase | + |
| Existence of quinone | MK-8 (H2) |
| Rod-coccus cycle | − |
| Extension of peripheral cells of colony | not observed |
| Growth under anaerobic condition | − |
| Diamino acid of cell wall | meso-diaminopimelic acid |
| Glycolyl test | + (glycolyl type) |
| Sugar composition of cell wall: | |
| Arabinose | + |
| Galactose | + |
| BC-20: | |
| Shape | bacillus |
| Gram's stain | − |
| Spore | − |
| Mobility | + |
| Flagellum | peripheral |
| Oxidase | + |
| Catalase | + |
| O-F test | alkalization |
| Production of 3-ketolactose | − |
| Existence of Quinone | Q-8 |

The above-described taxonomical properties were examined by referring to *Bergey's Manual of Systematic Bacteriology* (1986). As a result, the SK12 strain was identified to belong to the genus Enterobacter; the SK103 and HR1 strains to the genus Arthrobacter; the BC4 and BC23 strains to the genus Caseobacter; the SK150 strain to the genus Flavobacterium; the SK13, SK31, SK87, BC13-2 and BC15-2 strains to the genus Pseudomonas: the SK92, HR11 and SK70 strains to the genus Rhodococcus; and the BC20 strain to the genus Alcaligenes, respectively.

The present invention is explained further below by referring to a generally adopted embodiment.

Culture media which can be used for culturing the microorganisms according to the present invention usually contain assimilable carbon sources and nitrogen sources and inorganic nutrients necessary for growth. Carbon sources include glucose, glycerol and sucrose. Nitrogen sources include yeast extract, peptone and ammonium sulfate. Inorganic nutrients include dipotassium hydrogenphosphate, magnesium chloride and ferric chloride. It is preferable to obtain higher enzyme activity by adding nitriles (e.g., 2-chloropropionitrile, acetonitrile, propionitrile, n-butyronitrile, isobutyronitrile, benzonitrile, benzyl cyanide and 3-cyanopyridine) or, amides or lactams corresponding to those nitriles (e.g., $\epsilon$-caprolactam and $\gamma$-butyrolactam) to the culture in the initial or middle stage of culturing in such a concentration that does not impair greatly growth of the microorganism.

Culturing is conducted aerobically under controlled conditions selected according to the microorganism, i.e., at a pH of from 4 to 10 and at a temperature of from 20° to 90° C. for a period of from 24 to 96 hours.

The hydrolysis of DL-lactonitrile is carried out by bringing DL-lactonitrile into contact with the thus-obtained microbial cells or treated microbial cells (ruptured cells, crude or purified enzyme isolated therefrom, immobilized microbial cells or enzyme) in a polar solvent, whereby a desired optically active lactic acid, i.e., D- or L-lactic acid, is obtained from DL-lactonitrile in a predominant proportion (i.e., 50 to 100%) and in a high yield. Typical examples of usable polar solvents include water and an aqueous medium, e.g., physiologic saline and a phosphoric acid buffer solution. If desired, organic solvents, such as lower alcohols (e.g., methanol and ethanol), dimethylformamide and dioxane, may be used in combination with the polar solvent.

The hydrolysis reaction also can be carried out by using acetaldehyde and prussic acid in place of DL-lactonitrile.

DL-Lactonitrile usually is used at a concentration of from 0.01 to 10% by weight in the reaction system and the concentrations of acetaldehyde and prussic acid are 0.01 to 5% by weight and 0 005 to 3% by weight, respectively. The microbial cells usually are used in an amount of from 0.01 to 5% by weight (dry basis) based on DL-lactonitrile. The reaction is performed at a pH of from 3 to 12, and preferably from 6 to 10, and at a temperature of from the freezing point to 70° C., and preferably from 10° to 50° C. for a period of from 0.5 to 72 hours.

After the microbial cells are removed from the reaction system by centrifugation or the like means, the desired optically active lactic acid is isolated from the reaction solution by any of known techniques, such as concentration, electrical dialysis, ion exchange, extraction and crystallization.

According to the present invention, a desired optically active lactic acid can be prepared directly from DL-lactonitrile in a predominant proportion (50 to 100%). The present invention makes it feasible to convert stoichiometrically all the raw material to a desired optically active lactic acid, thus providing an extremely efficient process for preparing optically active lactic acids.

The present invention is now illustrated in greater detail with reference to the following Examples, but it should be understood that the present invention is not deemed to be limited thereto.

EXAMPLE 1

(1) Culturing

Each of the microorganisms shown in Table 1 below was inoculated into 10 ml of a medium having the following composition in a test tube (diameter: 22 mm) and shake-cultured at 30° C. for 2 days.

| Medium Composition: | |
|---|---|
| Glycerol | 20 g |
| Yeast extract | 3 g |
| 2-Chloropropionitrile | 1 g |
| $K_2HPO_4$ | 3 g |
| $MgCl_2$ | 0.2 g |
| $CaCl_2$ | 40 mg |
| $MnSO_4 \cdot 4H_2O$ | 4 mg |
| $FeCl_3 \cdot 7H_2O$ | 0.7 mg |
| $ZnSO_4 \cdot 7H_2O$ | 0.1 mg |
| Distilled water | 1000 ml |

-continued

| Medium Composition: | |
|---|---|
| pH | 7.2 |

(2) Hydrolysis of DL-Lactonitrile

The microbial cells were collected from each culture by centrifugation and washed with a 30 mM phosphoric acid buffer solution (pH=7.0). The precipitated cells were collected and resuspended in 5 ml of the same buffer solution. DL-Lactonitrile was added to the cell suspension in a final concentration of 10 mM, followed by incubation at 30° C. for 24 hours. After completion of the reaction, the system was subjected to centrifugation to remove the microbial cells. The supernatant liquor was analyzed by column chromatography using a matrix, "MCI-GEL-CRS10W", produced by Mitsubishi Chemical Co., Ltd. or by an enzyme analysis using D-or L-lactic acid dehydrogenase and nicotinamide adenine dinucleotide to determine the optically active lactic acid produced and its optical purity. The results obtained are shown in Table 1.

TABLE 1

| Microorganism | | Amount of Microbial Cells | Optical Purity* | Yield |
|---|---|---|---|---|
| Genus | Strain | OD 630 nm | (% ee) | (%) |
| Enterobacter | SK121 | 12.4 | 100.0 | 98.0 |
| | JCM 3943 | 38.6 | 100.0 | 20.0 |
| Arthrobacter | SK103 | 33.8 | 27.0 | 85.0 |
| | IFO 12138 | 42.0 | −29.1 | 79.0 |
| | HR1 | 31.0 | −100.0 | 8.5 |
| Caseobacter | BC4 | 15.8 | 52.0 | 87.5 |
| | BC23 | 20.6 | 51.7 | 21.4 |
| Brevibacterium | IAM 1790 | 22.5 | 31.0 | 87.0 |
| | ATCC 11822 | 16.3 | −100.0 | 11.4 |
| Aureobacterium | IAM 1561 | 15.3 | −100.0 | 51.6 |
| Escherichia | IFO 3301 | 17.7 | 85.7 | 70.0 |
| Micrococcus | ATCC 383 | 20.6 | −100.0 | 96.0 |
| | IAM 1099 | 20.5 | −71.0 | 91.6 |
| | IFO 3768 | 57.0 | −100.0 | 24.3 |
| Streptomyces | IFO 3355 | 24.1 | 85.3 | 95.6 |
| | IFO 14059 | 3.5 | 26.0 | 19.0 |
| Flavobacterium | ATCC 8315 | 33.0 | 67.6 | 92.5 |
| | SK150 | 12.1 | 20.0 | 36.9 |
| Aeromonas | IFO 13288 | 26.5 | 88.0 | 55.3 |
| Nocardia | KCC A0191 | 20.9 | −55.2 | 69.6 |
| | IFM 19 | 6.5 | −100.0 | 60.0 |
| Mycoplana | ATCC 4279 | 14.5 | −100.0 | 25.0 |
| Cellulomonas | IAM 12107 | 31.0 | −100.0 | 97.2 |
| Erwinia | IFO 12686 | 21.4 | 37.4 | 94.6 |
| Candida | IFO 0566 | 23.0 | 93.5 | 62.0 |
| | IAM 4964 | 81.2 | −100.0 | 3.0 |
| Pseudomonas | SK13 | 12.7 | 69.8 | 69.6 |
| | SK31 | 16.1 | 53.3 | 58.2 |
| | SK87 | 19.6 | 81.5 | 56.2 |
| | BC13−2 | 38.8 | 36.3 | 33.5 |
| | IAM 12356 | 8.9 | 71.1 | 36.9 |
| | IAM 1267 | 9.3 | −100.0 | 4.1 |
| | IAM 1002 | 37.2 | 100.0 | 67.0 |
| | BC15−2 | 33.5 | 100.0 | 86.0 |
| Rhodococcus | IFO 12540 | 23.9 | 25.4 | 100.2 |
| | IFO 12320 | 22.2 | −92.6 | 81.0 |
| | SK92 | 17.2 | −72.5 | 69.8 |
| | SK70 | 15.3 | −10.0 | 98.5 |
| | HR11 | 28.1 | −23.5 | 91.9 |
| | IFM 132 | 35.6 | −90.0 | 48.0 |
| | IFO 12538 | 24.6 | −61.0 | 80.0 |
| | IFM 155 | 45.7 | −100.0 | 67.0 |
| Rhodococcus | IFO 12539 | 25.0 | −87.0 | 88.0 |
| | ATCC 12674 | 18.2 | −56.0 | 95.0 |
| Bacillus | IFO 12197 | 17.8 | −100.0 | 8.9 |
| | ATCC 25833 | 67.2 | −100.0 | 65.0 |
| | ATCC 21697 | 7.3 | −100.0 | 8.9 |
| | IFO 12199 | 18.6 | −100.0 | 63.0 |

TABLE 1-continued

| Microorganism | | Amount of Microbial Cells | Optical Purity* | Yield |
|---|---|---|---|---|
| Genus | Strain | OD 630 nm | (% ee) | (%) |
| Alcaligenes | BC20 | 18.2 | 100.0 | 2.1 |
| Corynebacterium | IAM 1642 | 33.1 | −100.0 | 100.0 |
| Microbacterium | IAM 1640 | 26.3 | −100.0 | 91.0 |
| Obsumbacterium | ATCC 12841 | 8.1 | −100.0 | 4.7 |

Note:
*Optical purity is based on D-lactic acid. 100% ee indicates that the compound solely comprises D-lactic acid, and −100% ee indicates that the compound solely comprises L-lactic acid.

EXAMPLE 2

(1) Culturing

Enterobacter sp. SK12 was cultured in the same manner as in Example 1, except for using 100 ml of the medium in a 500 ml volume Erlenmeyer flask.

(2) Hydrolysis of DL-Lactonitrile

To the microbial cells collected from the culture in the same manner as in Example 1 was added 50 mM phosphoric acid buffer solution to prepare a cell suspension having a cell concentration of 30 (OD 630 nm). To the cell suspension was added DL-lactonitrile to a final concentration of 20 mM, and the reaction progress was observed over time. A 2 ml sample of the reaction system was taken out each 1 hour to determine the amount of lactic acid produced in the same manner as in Example 1. The results obtained are shown in Table 2 below.

TABLE 2

| Reaction Time (hr) | Yield of Product | |
|---|---|---|
| | D-Lactic Acid (%) | L-Lactic Acid (%) |
| 1.0 | 27.5 | 0 |
| 2.0 | 60.0 | 0 |
| 3.0 | 80.0 | 0 |
| 4.0 | 97.5 | 0 |

EXAMPLE 3

(1) Culturing

Enterobacter sp. SK12 was cultured in the same manner as in Example 2.

(2) Hydrolysis using Acetaldehyde and Prussic Acid

To the microbial cells collected from the culture in the same manner as in Example 2 was added 50 mM phosphoric acid buffer solution to prepare a cell suspension having a cell concentration of 30 (OD 630 nm). To the cell suspension was added acetaldehyde and prussic acid to a final concentration of 20 mM, respectively, and the reaction was carried out at 30° C. for 5 hours. The amount of lactic acid produced and its optical purity were determined in the same manner as in Example 1. The results obtained are shown in the Table 3 below.

TABLE 3

| Reaction Time (hr) | Yield of Lactic Acid (%) | Optical Purity of D-Lactic Acid (% ee) |
|---|---|---|
| 5 | 83 | 100 |

What is claimed is:

1. A process for preparing an optically active lactic acid comprising subjecting DL-lactonitrile to the action of a microorganism selected from the group consisting of Enterobacter sp. SK12 (FERM No. BP-3322), *Enterobacter taylorae* JCM 3943, Arthrobacter sp. SK103 (FERM No. P-11300), Arthrobacter sp. HR1 (FERM No. BP-3323), *Arthrobacter oxydans* IFO 12138, Caseobacter sp. BC4 (FERM No. BP-3316), Caseobacter sp. BC23 (FERM No. P-11261), *Brevibacterium acetylicum* IAM 1790, *Brevibacterium helvolum* ATCC 11822, *Aureobacterium testaceum* IAM 1561, *Escherichia coli* IFO 3301, *Micrococcus luteus* ATCC 383, *Micrococcus varians* IAM 1099, *Micrococcus roseus* IFO 3768, *Streptomyces griseus* IFO 3355, *Streptomyces griseus* IFO 14059, *Flavobacterium flavescens* ATCC 8315, Flavobacterium sp. SK150 (FERM No. P-11645), *Aeromonas punctata* IFO 13288, *Nocardia calcarea* KCC A0191, *Nocardia polychromogenes* IFM 19, *Mycoplana dimorcha* ATCC 4279, *Cellulomonas fimi* IAM 12107, *Erwinia herbicola* IFO 12686, *Candida guilliermondii* IFO 0566, *Candida lypolytica* IAM 4964, Pseudomonas sp. SK13 (FERM No. BP-3325), Pseudomonas sp. SK31 (FERM No. P-11310), Pseudomonas sp. SK87 (FERM No. P-11311), Pseudomonas sp. BC13-2 (FERM No. BP-3319), Pseudomonas sp. BC15-2 (FERM No. BP-3320), *Pseudomonas synxantha* IAM 12356, *Pseudomonas aerucinosa* IAM 1267, *Pseudomonas ovalis* IAM 1002, *Rhodococcus erythropolis* IFO 12540, *Rhodococcus erythropolis* IFO 12320, Rhodococcus sp. SK92 (FERM No. BP-3324), Rhodococcus sp. HR11 (FERM No. P-11306), Rhodococcus sp. SK70 (FERM No. P-11304), *Rhodococcus erythropolis* IFO 12538, *Rhodococcus erythropolis* IFO 12539, *Rhodococcus erythropolis* IFM 132, *Rhodococcus erythropolis* IFM 155, *Rhodococcus rhodochrous* ATCC 12674, *Bacillus licheniformis* IFO 12197, *Bacillus licheniformis* IFO 12199, *Bacillus mecaterium* ATCC 25833, *Bacillus subtilis* ATCC 21697, Alcaligenes sp. BC20 (FERM No. P-11264), *Corynebacterium flavescens* IAM 1642, *Microbacterium lacticum* IAM 1640 and *Obsumbacterium proteus* ATCC 12841, wherein said microorganism may be ruptured or immobilized; or subjecting DL-lactonitrile to the action of crude, purified or immobilized enzyme obtained from said microorganism, wherein said microorganism or said enzyme stereospecifically hydrolyzes a nitrile in a polar solvent to produce directly D-lactic acid or L-lactic acid in a predominant proportion to said starting DL-lactonitrile.

2. A process for preparing an optically active lactic acid comprising subjecting acetaldehyde and prussic acid to the action of a microorganism selected from the group consisting of Enterobacter sp. SK12 (FERM No. BP-3322), *Enterobacter taylorae* JCM 3943, Arthrobacter sp. SK103 (FERM No. P-11300), Arthrobacter sp. HR1 (FERM No. BP-3323), *Arthrobacter oxydans* IFO 12138, Caseobacter sp. BC4 (FERM No. BP-3316), Caseobacter sp. BC23 (FERM No. P-11261), *Brevibacterium acetylicum* IAM 1790, *Brevibacterium helvolum* ATCC 11822, *Aureobacterium testaceum* IAM 1561, *Escherichia coli* IFO 3301, *Micrococcus luteus* ATCC 383, *Micrococcus varians* IAM 1099, *Micrococcus roseus* IFO 3768, *Strectomyes griseus* IFO 3355, *Streptomyes griseus* IFO 14059, *Flavobacterium flavescens* ATCC 8315, Flavobacterium sp. SK150 (FERM No. P-11645), *Aeromonas punctata* IFO 13288, *Nocardia calcarea* KCC A0191, *Nocardia polychromogenes* IFM 19, *Mycoplana dimorpha* ATCC 4279, *Cellulomonas fimi* IAM 12107, *Erwinia herbicola* IFO 12686, *Candida guilliermondii* IFO 0566, *Candida lypolytica* IAM 4964, Pseudomonas sp. SK13 (FERM No. BP-3325), Pseudomonas sp. SK31 (FERM No. P-11310), Pseudomonas sp. SK87 (FERM No. P-11311), Pseudomonas sp. BC13-2 (FERM No. BP-3319), Pseudomonas sp. BC15-2 (FERM No. BP-3320), *Pseudomonas synxantha* IAM 12356, *Pseudomonas aerucinosa* IAM 1267, *Pseudomonas ovalis* IAM 1002, *Rhodococcus erythropolis* IFO 12540, *Rhodococcus erythropolis* IFO 12320, Rhodococcus sp. SK92 (FERM No. BP-3324), Rhodococcus sp. HR11 (FERM No. P-11306), Rhodococcus sp. SK70 (FERM No. P-11304), *Rhodococcus erythropolis* IFO 12538, *Rhodococcus erythropolis* IFO 12539, *Rhodococcus erythropolis* IFM 132, *Rhodococcus erythropolis* IFM 155, *Rhodococcus rhodochrous* ATCC 12674, *Bacillus licheniformis* IFO 12197, *Bacillus licheniformis* IFO 12199, *Bacillus mecaterium* ATCC 25833, *Bacillus subtilis* ATCC 21697, Alcaligenes sp. BC20 (FERM No. P-11264), *Corynebacterium flavescens* IAM 1642, *Microbacterium lacticum* IAM 1640 and *Obsumbacterium proteus* ATCC 12841, wherein said microorganism may be ruptured or immobilized; or subjecting DL-lactonitrile to the action of crude, purified or immobilized enzyme obtained from said microorganism, wherein said microorganism or said enzyme stereospecifically hydrolyzes a nitrile in a polar solvent to produce directly D-lactic acid or L-lactic acid in a predominant proportion to said acetaldehyde and prussic acid.

3. The process of claim 1, wherein said Enterobacter sp. SK12 (FERM No. BP-3322), Arthrobacter sp. SK103 (FERM No. P-11300), Arthrobacter sp. HR1 (FERM No. BP-3323), Caseobacter sp. BC4 (FERM No. BP-3316), Caseobacter sp. BC23 (FERM No. P-11261), Flavobacterium sp. SK150 (FERM No. P-11645), Pseudomonas sp. SK13 (FERM No. BP-3325), Pseudomonas sp. SK31 (FERM No. P-11310), Pseudomonas sp. SK87 (FERM No. P-11311), Pseudomonas sp. BC13-2 (FERM No. BP-3319), Pseudomonas sp. BC15-2 (FERM No. BP-3320), Rhodococcus sp. SK92 (FERM No. BP-3324), Rhodococcus sp. HR11 (FERM No. P-11306), Rhodococcus sp. SK70 (FERM No. P-11304), Alcaligenes sp. BC20 (FERM No. P-11264), or a variant of those strains.

4. The process of claim 1, wherein said polar solvent is water, physiologic saline or a phosphoric acid buffer solution.

5. The process of claim 2, wherein said microorganism is Enterobacter sp. SK12 (FERM No. BP-3322), Arthrobacter sp. SK103 (FERM No. P-11300), Arthrobacter sp. HR1 (FERM No. BP-3323), Caseobacter sp. BC4 (FERM No. BP-3316), Caseobacter sp. BC23 (FERM No. P-11261), Flavobacterium sp. SK150 (FERM No. P-11645), Pseudomonas sp. SK13 (FERM No. BP-3325), Pseudomonas sp. SK31 (FERM No. P-11310), Pseudomonas sp. SK87 (FERM No. P-11311), Pseudomonas sp. BC13-2 (FERM No. BP-3319), Pseudomonas sp. BC15-2 (FERM No. BP-3320), Rhodococcus sp. SK92 (FERM No. BP-3324), Rhodococcus sp. HR11 (FERM No. P-11306), Rhodococcus sp. SK70 (FERM No. P-11304), Alcaligenes sp. BC20 (FERM No. P-11264), or a variant of those strains.

* * * * *